United States Patent
Sevenster et al.

(10) Patent No.: US 11,488,698 B2
(45) Date of Patent: Nov. 1, 2022

(54) FACILITATED STRUCTURED MEASUREMENT MANAGEMENT TOOL PROGRESS AND COMPLIANCE ANALYTICS SOLUTION

(71) Applicants: KONINKLIJKE PHILIPS N.V., Eindhoven (NL); UNIVERSITY OF CHICAGO SCHOOL OF MEDICINE (UCM), Chicago, IL (US)

(72) Inventors: Merlijn Sevenster, Haarlem (NL); Paul Joseph Chang, Chicago, IL (US)

(73) Assignees: KONINKLIJKE PHILIPS N.V., Eindhoven (NL); UNIVERSITY OF CHICAGO SCHOOL OF MEDICINE (UCM), Chicago, IL (US)

( * ) Notice: Subject to any disclaimer, the term of this patent is extended or adjusted under 35 U.S.C. 154(b) by 652 days.

(21) Appl. No.: 16/312,390

(22) PCT Filed: Jun. 13, 2017

(86) PCT No.: PCT/EP2017/064331
§ 371 (c)(1),
(2) Date: Dec. 21, 2018

(87) PCT Pub. No.: WO2017/220367
PCT Pub. Date: Dec. 28, 2017

(65) Prior Publication Data
US 2019/0206535 A1 Jul. 4, 2019

Related U.S. Application Data

(60) Provisional application No. 62/353,582, filed on Jun. 23, 2016.

(51) Int. Cl.
*G16H 15/00* (2018.01)
*G16H 40/20* (2018.01)
(Continued)

(52) U.S. Cl.
CPC .............. *G16H 15/00* (2018.01); *G06F 40/18* (2020.01); *G16H 10/60* (2018.01); *G16H 30/20* (2018.01); *G16H 40/20* (2018.01)

(58) Field of Classification Search
CPC ........ G16H 15/00; G16H 30/20; G16H 10/60; G16H 40/20; G06F 40/18
(Continued)

(56) References Cited

U.S. PATENT DOCUMENTS

2007/0179811 A1  8/2007  Reiner
2015/0154530 A1* 6/2015  Felix .............. G06Q 10/063114
                                                            705/7.15
(Continued)

FOREIGN PATENT DOCUMENTS

WO   WO-2012033771 A2 *  3/2012  ......... G06F 19/3431

OTHER PUBLICATIONS

El-Zahraa et al., Current Trends in Medical Image Registration and Fusion, Oct. 21, 2015, Egyptian Informatics Journal 17, pp. 99-124, http://dx.doi.org/10.1016/j.eij.2015.09.002 (Year: 2015).*

(Continued)

*Primary Examiner* — Joy Chng

(57) ABSTRACT

A method and arrangement for determining measurements that need to be registered are disclosed. The method retrieves a plurality of clinical reports, detects a measurement in each of the plurality of clinical reports, and determines which of the detected measurements have been registered in a defined structured format. A method also identifies a plurality of patients with scheduled future clinical exam, determines if any of the plurality of patients have measurements that require registration and places the plurality of patients with the measurements requiring registration on a worklist. A further method retrieves data for a plurality of patients, determines whether each of the patients (Continued)

have new measurements, determines, for each of the patients, whether the new measurements have been registered, identifies a radiologist for each of the new measurements and generates a compliance scorecard for each of the radiologists.

13 Claims, 5 Drawing Sheets

(51) Int. Cl.
   *G16H 10/60* (2018.01)
   *G06F 40/18* (2020.01)
   *G16H 30/20* (2018.01)
(58) Field of Classification Search
   USPC .......................................................... 705/2–3
   See application file for complete search history.

(56) References Cited

U.S. PATENT DOCUMENTS

2016/0012319 A1* 1/2016 Mabotuwana ......... G16H 15/00
                                                            382/128
2016/0253468 A1* 9/2016 Osawa ................... G16H 30/20
                                                            600/407

OTHER PUBLICATIONS

Folio et al., Quantitative Radiology Reporting in Oncology: Survey of Oncologists and Radiologists, Sep. 2015, American Journal of Roentgenology, vol. 205, No. 3, pp. W233-W243, http://ajronline.org/doi/full/10.2214/AJR.14.14054 (Year: 2015).*
Johnson et al., Machine Learning and Decision Support in Critical Care, Feb. 2016, Proc. IEEE Inst Elect Electro Eng., 104(2), pp. 444-466, doi: 10.1109/JPROC (Year: 2016).*
Yetisgen-Yildiz, M. et al., "Automatic identification of critical follow-up recommendation sentences in radiology reports." AMIA Annu Symp Proc. 2011; 2011: 1593-1602. Published online Oct. 22, 2011.
Gerstmair, A. et al., "Intelligent image retrieval based on radiology reports." European Society of Radiology (2012) 22:2750-2758.
Roberts, K. et al., "A machine learning approach for identifying anatomical locations of actionable findings in radiology reports." AMIA Annu Symp Proc 2012: 2012: 779-788. Published online Nov. 3, 2012.
Hassanpour, S. et al., "Information extraction from multi-institutional radiology reports." Artificial Intelligence in Medicine, vol. 66, Jan. 2016, pp. 29-39.
Sevenster, M. et al., "Improved efficiency in clinical workflow of reporting measured oncology lesions via PACS-integrated lesion tracking tool,". Am J Roentgenol, Mar. 2015, p. 576-.583.
Sevenster, M. et al., "Natural language processing techniques for extracting and categorizing finding measurements in narrative radiology reports,". Appl Clin Inf., vol. 6, No. 3, pp. 600-610, 2015.

* cited by examiner

FACILITATED STRUCTURED MEASUREMENT MANAGEMENT TOOL PROGRESS AND COMPLIANCE ANALYTICS SOLUTION

CROSS-REFERENCE TO PRIOR APPLICATIONS

This application is the U.S. National Phase application under 35 U.S.C. § 371 of International Application No. PCT/EP2017/064331, filed on Jun. 13, 2017, which claims the benefit of U.S. Patent Application No. 62/353,582, filed on Jun. 23, 2016. These applications are hereby incorporated by reference herein.

BACKGROUND

During a doctor's visit, a person may undergo an imaging scan as part of a checkup. The imaging scan may be an X-ray scan, a Computer Tomography (CT) scan, a magnetic resonance imaging (MRI) scan, an ultrasound scan, etc. Radiologists will review these imaging scans from a Picture Archive and Communications System (PACS) or otherwise and record their observations. Depending on the type of scan or the results of the scan, the observations will travel downstream to an appropriate doctor or specialist, such as to an oncologist in the case of a cancerous lesion being identified by a CT scan.

SUMMARY

The exemplary embodiments relate to a method and system for determining measurements that need to be registered.

According to an aspect of the present disclosure, the method and system retrieves a plurality of clinical reports, detects a measurement in each of the plurality of clinical reports, and determines which of the detected measurements have been registered in a defined structured format.

In another aspect, the method and system classify the detected measurements, wherein the classifying determines a temporality of the one or more measurements, wherein the temporality determines whether each of the measurements are from a current imaging scan or a previous imagining scan. The classifying may be conducted by statistical or machine learning methods. The detecting may be applied to at least one of a plurality of selected sections of the clinical reports.

In another aspect, the clinical reports are retrieved for a plurality of patients. The retrieving may be based on a selected time frame.

In another aspect, the method and system calculates a ratio of a number of the measurements that require registration to a total number of the measurements. Additionally, the method and system calculates a ratio of patients with measurements requiring registration to a total number of patients with measurements.

In another aspect, the registration comprises utilizing a registration program capable to formatting the measurements into a structured format. The measurements may be lesion measurements.

In a further aspect, a method and system identifies a plurality of patients with scheduled future clinical exam, determines if any of the plurality of patients have measurements that require registration, and places the plurality of patients with the measurements requiring registration on a worklist.

In another aspect, the identifying is narrowed by a time period within which the future clinical exams are scheduled. The worklist may be a spreadsheet file.

In another aspect, the method and system registers the measurements of the plurality of patients on the worklist. The registering may be done manually or automatically. The method and system further validates the registering, wherein the validating comprises a database to confirm that the measurement are in a structured format.

In a further aspect, a method and system retrieves data for a plurality of patients, determines whether each of the patients have new measurements, determines, for each of the patients, whether the new measurements have been registered, identify a radiologist for each of the new measurements, and generates a compliance scorecard for each of the radiologists.

In another aspect, the plurality of patients comprises only the patients that have been bootstrapped.

In another aspect, the compliance scorecards are available for public or private viewing on a display. The compliance scorecards may comprise scores, wherein each of the scores is anonymized except for a viewing radiologist's score.

DETAILED DESCRIPTION

Figure 1:
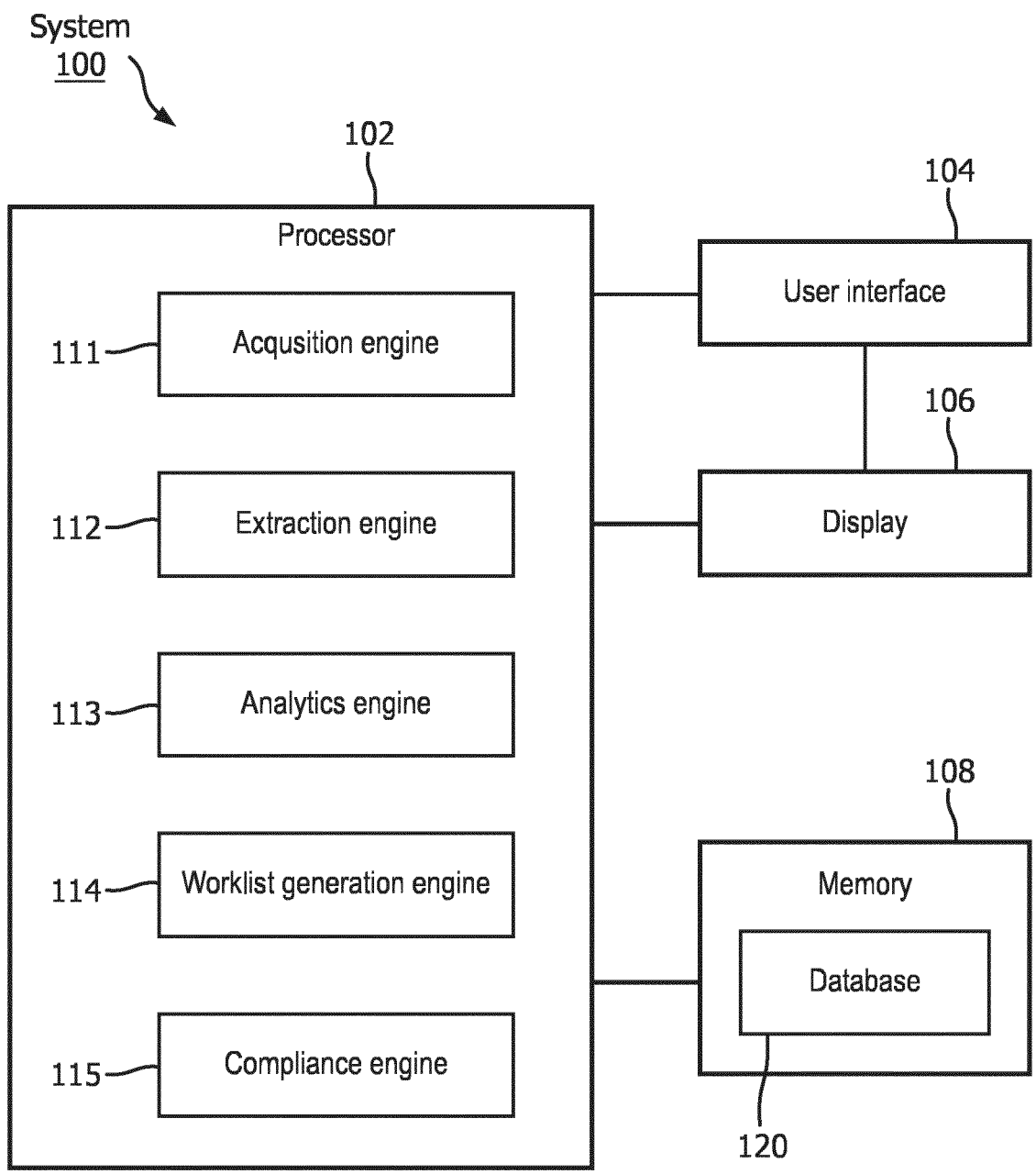
FIG. 1 shows a schematic drawing of a system according to an exemplary embodiment.

The exemplary embodiments may be further understood with reference to the following description and the appended drawings, wherein like elements are referred to with the same reference numerals. The exemplary embodiments relate to systems and methods for assessing a user's progress to register measurements from a patient's prior clinical exams before the patient's future clinical exam. The measurement refers to an evaluation of an object discovered on an imaging scan, such as a lesion, tumor, abscess, etc., and may be recorded on a clinical report. Throughout the remainder of this description, the term "lesion" will be used to describe the object that is to be evaluated, but those skilled in the art will understand that the exemplary embodiments can be applicable to other types of objects. The imaging scan may be, but is not limited to, a radiological scan, an X-ray scan, a magnetic resonance imaging (MRI) scan, an ultrasound scan, a position emission tomography (PET) scan, a computerized tomography (CT) scan, or any other kind of imaging scan. The user may be a radiologist, a group of radiologists or any other person or group qualified to read the imaging scans from a Picture Archive and Communications System (PACS) or imaging system workstation.

The PACS is a workstation that aids radiologists in their duties and allows them to keep up with ever increasing workloads. In particular, the PACS employs an intuitive graphical user interface that provides access to a patient's radiological history, including diagnostic reports, exam notes, clinical history and imaging scans. Further, the PACS has several features that simplify and speed up workflow. These features are critical in improving the radiologist's productivity.

As part of the PACS workflow or the imaging system workstation's workflow, the measurements may be registered using a registration program within the PACS or the imaging system workstation, such as a measurement assistant tool (e.g. Measurement Assistant distributed by Philips). The measurement assistant tool will streamline the workflow of the PACS or the imaging system workstation by, for example, recording measurements, offering quick navigation to imaging scans with measurements and creating an easily accessible table of results. Further, the exemplary embodiments relate to systems and methods for creating a bootstrapping worklist of cases that require the prior measurements to be registered. Exemplary embodiments may make reference to the process of registering the prior measurements as bootstrapping.

Thus, it can be seen that the exemplary embodiments address a problem that is rooted in computer technology. Specifically, the issue of registration of imaging scans did not exist prior to the ability to store the imaging exams in the memory of a computing device and store the data associated with the imaging exams in the computing device. Among other things, the exemplary embodiments solve the problem of registration of the imaging exams by encouraging and tracking the use of the registration of imaging scans by medical professionals. Further, the exemplary embodiments significantly improve the productivity and efficiency of the radiologists. As discussed above and will be further discussed below, the improvements to the productivity and efficiency of the radiologists is vital to both medical institutions and patients, alike, due to the constant rise in radiologist workloads.

Quantitative imaging relies on the structured collection of reusable quantitative data points that are obtained in the course of radiologic interpretations. As described above, one manner of collecting and managing these data points is by using the measurement assistant tool. The measurement assistant tool is a tool used in PACS workflow and may collect and manage these data points by saving the data points in a structured format. The exact details of the structured format is not relevant to the exemplary embodiments, but rather the concept that the data points are stored and persisted in a consistent manner is an advantage of the measurement assistant tools. These measurement assistant tools may be used to save time and effort by radiologists because the measurement assistant tool may obviate the need to dictate the lesion measurement reports into a narrative format. Once the data points are obtained using the measurement management tool, these data points may be persisted in the structured format for use in any number of downstream applications that may be used to aid in the treatment of the patient.

However, for the advantages of the measurement assistant tools to be realized, the radiologists in a particular department should consistently use the available measurement assistant tool. This may not be the case, however, because there is an upfront cost (in terms of time and effort) associated with using the measurement assistant tool. This upfront cost may be described in the following manner. The measurement assistant tools may be described as having two modes of operation, a baseline mode and a follow-up mode. The baseline mode may be considered to be the occasion when there have been no measurements that have been entered for a particular patient, whether this is the patient's first imaging scan or a subsequent imaging scan. On this occasion, the radiologist may have to use the measurement assistant tool to create new lesion objects for each lesion that the radiologist desires to follow. This identification, naming and measurement of the target lesions may be more time consuming than the standard manner of dictating measurements in the narrative format. Thus, some radiologists may be reluctant to adopt the measurement assistant tool because of this upfront effort. On the other hand, in the follow-up mode, when all lesion objects have been annotated, the measurements from the current exam simply have to be added to the pre-existing lesion objects that were previously created and stored. Experiments have shown that this follow-up mode is much more time efficient than the standard manner of dictating measurements in the narrative format. Moreover, since there are typically many more follow-up imaging scans than initial imaging scans, the initial upfront effort in baseline mode saves much more time during the course of the patient's treatment having many follow-up imaging scans. In addition, the structured format of the data points provided by the measurement assistant tool provide a more consistent manner of evaluating the lesions by downstream physicians, e.g., oncologists.

Despite these obvious advantages of using the measurement assistant tools, it is still an effort to convince radiologists and radiology departments to adopt the measurement assistant tools. The exemplary embodiments described herein are designed to aid radiology departments to adopt the measurement assistant tools and to track the adoption and usage of the measurement assistant tools.

Prior to describing the exemplary embodiments, several use cases will be described to provide context for the implementation of the exemplary embodiments. In a first exemplary use case, a patient may be scheduled for an imaging scan in the two days. The patient may be a new patient, e.g., this is the first imaging scan that the patient is undergoing. This is the most simple use case because as described above, in an ideal situation, the radiologist will use the measurement assistant tool in the baseline mode and create new lesion objects for each lesion that the radiologist desires to follow. In this use case, the exemplary embodiments may be used to determine if the radiologist did, in fact, use the measurement assistant tool when analyzing the imaging scan. The exemplary embodiments may also be used to identify individual radiologists and their statistics with respect to using the measurement assistant tool.

In a second exemplary use case, a second patient may be scheduled for an imaging scan in two days. The second patient may be a patient that has undergone one or more previous imaging scans. In the ideal situation, the one or more previous imaging scans will have been registered with the measurement assistant tool and the current imaging scan will be analyzed by the radiologist using the measurement assistant tool in the follow-up mode. However, in many situations, the one or more previous imaging scans have not been registered. The exemplary embodiments may be used to identify the one or more previous imaging scans that have not been registered as priority registration or bootstrapping cases so that they may be registered prior to the upcoming imaging scan for the second patient. The exemplary embodiments may also be used to perform the registration for the one or more previous imaging scans. It should be understood that if the registration of the one or more previous imaging scans is completed prior to the analysis of the current imaging scan for the second patient, the radiologist may then be able to use the measurement assistant tool in the follow-up mode for the analysis.

In a final exemplary use case, the radiology department may have many imaging scans that are not registered. This may be because the radiologists have numerous imaging scans as part of their workflow from many different patients. Since efficiency is very important for the radiologists, a major challenge in radiology is to improve workflow efficiency so that the radiologists can register as many imaging scans as possible. Greater efficiency would lead to faster reporting of critical findings, lower rescan rates, more uniformity in imaging scans, clearer actionable reports, enhanced patient experience, and improvements to reimbursements. The exemplary embodiments may identify these imaging scans that are not registered, prioritize the imaging scans that should be registered (e.g., create a bootstrapping worklist) and register the imaging scans such that the radiologists, when analyzing subsequent imaging scans for particular patients may be able to use the measurement assistant tool in the follow-up mode. Thus, the exemplary embodiments would have a significant impact on the efficiency of the radiologists.

As shown in FIG. 1, a system 100, according to an exemplary embodiment of the present disclosure, is used to perform the exemplary functionalities that were described above. The system 100 comprises a processor 102, a user interface 104, a display 106, and a memory 108. Each of the components of the system 100 may include various hardware implementations. For example, the processor 102 may be hardware component that comprises circuitry necessary to interpret and execute electrical signals fed into the system 100. Examples of processors 102 include central processing units (CPUs), control unit, microprocessor, etc. The circuitry may be implemented as an integrated circuit, an application specific integrated circuit (ASIC), etc. The user interface 104 may be, for example, a keyboard, a mouse, a keypad, a touchscreen, etc. The display 106 may be a liquid crystal display (LCD) device, a light emitting diode (LED) display, an organic LED (OLED) display, a plasma display panel (PDP), etc. Those skilled in the art will understand that the functionalities of the user interface 104 and display 106 may be implemented in a single hardware component. For example, a touchscreen device may be used to implement both the display 106 and the user interface 104. The memory 108 may be any type of semiconductor memory, including volatile and non-volatile memory. Examples of non-volatile memory include flash memory, read only memory (ROM), programmable ROM (PROM), erasable PROM (EPROM) and electrically erasable PROM (EEPROM). Examples of volatile memory include dynamic random-access memory (DRAM), and fast CPU cache memory, which is typically static random-access memory (SRAM).

The memory 108 includes a database 120. The database 120 may store records correlating to the patients, the imaging scans, and the measurements. The records may include the clinical report composed by a patient's physician. Those of skill in the art will understand that the clinical report may be written, oral or a combination of both.

In an exemplary embodiment, the patient may be linked to a patient identifier. The patient identifier may be any type of an identification code, such as a Medical Record Number (MRN) or a Patient Identifier, used to identify the patient. The patient identifiers may also be stored in the database 120. The database 120 may be structured (e.g. in a structured format) in a manner that allows for patient specific queries. It should also be understood that the database 120 may represent a series of databases or other types of storage mechanisms that are distributed throughout system 100 or other interconnected systems.

The processor 102 may be implemented with engines, including, for example, an acquisition engine 111, an extraction engine 112, an analytics engine 113, a worklist generation engine 114 and a compliance engine 115. Each of these engines will be described in greater detail below. Those skilled in the art will understand that the engines 111-115 may be implemented by the processor 102 as, for example, lines of code that are executed by the processor 102, as firmware executed by the processor 102, as a function of the processor 102 being an application specific integrated circuit (ASIC), etc.

The acquisition engine 111 retrieves the clinical reports of the patient. The clinical reports may be retrieved, for example, by transmitting the patient's unique identifier through an Application Programming Interface (API) of a repository that contains the clinical reports, such as the PACS. In addition, a master list of the patients' unique identifiers may be retrieved via the API, which may be narrowed by a time frame. For example, only the patient idenfiers for the patients that received clinical exams between a time frame A and a time frame B may be retrieved. Alternatively, the clinical reports may be retrieved from the database 120. It will be understood by those skilled in the art that similar methods of retrieving the patients' records from the API may be utilized in retrieving the patients' records from the database 120.

The extraction engine 112 detects specified data in the clinical report. For example, in an exemplary embodiment, the extraction engine 112 may detect a number of measurements, such as lesions, recorded or described in the clinical report. Various techniques employed by the extraction engine 112 will be described in greater detail below.

The analytics engine 113 correlates the data provided by the extraction engine 112 with data retrieved from the database 120 to determine the number of measurements needed to be registered. In an exemplary embodiment, the analytics engine 113 assess the clinical report of a most recent clinical exam of the patient and detects the number of measurements made during that clinical exam. In particular, the analytics engine 113 may ignore measurements that are associated with certain temporalities (e.g. prior, previous, etc.) to accurately determine the measurements pertaining only to the most recent clinical exam.

Next, the analytics engine 113 may receive, from the database 120, a measurements count from a clinical report of a clinical exam performed before the most recent clinical exam. The analytics engine 113 then calculates the difference between the measurements count retrieved from the database 120 and the measurements detected from the clinical report of the most recent clinical exam. The resulting difference is the number of measurements needed to be registered. For example, if the analytics engine 113 counts four measurements (e.g. lesions) from the clinical report of the most recent clinical exam and two measurements from the clinical report of the clinical exam performed before the most recent clinical exam, then the number of measurements needed to be registered is two. It will be apparent to those skilled in the art that a difference of zero means that no measurements need to be registered for the patient.

The worklist generation engine 114 generates the bootstrapping worklist of cases where the patients have scheduled future clinical exams but have yet had the measurements from the most recent clinical exam registered. In particular, the worklist generation engine 114 retrieves the patients (e.g. via the patient identifiers) that have their scheduled future clinical exam within a certain time period. The time period may be a certain number of days, weeks, etc. For each of the patients, the worklist generation engine 114 consults the extraction engine 112 and the database 120 to verify if the patient has measurements that have been registered. If the worklist generation engine 114 determines that the patient has measurements that have not been registered, the patient identifier is placed on the bootstrapping worklist. The bootstrapping worklist, for example, may be a spreadsheet file. In an exemplary embodiment, the worklist generation engine 114 may continuously monitor for discrepancies between the extraction engine 112 and the measurements database 120 so as to update the bootstrapping worklist in real time.

The compliance engine 115 tracks compliance with the registration program. In particular, the compliance engine 115 consults the database 120 to validate that all of the measurements have been registered in the structured format. The structured format may be a format utilized by the registration program. In one variant, the compliance engine 115 may track the compliance after all of the cases have been bootstrapped from the bootstrapping list. In another variant, the compliance engine 115 may track the compliance after every time a case from the bootstrapping worklist has been bootstrapped.

Figure 2:
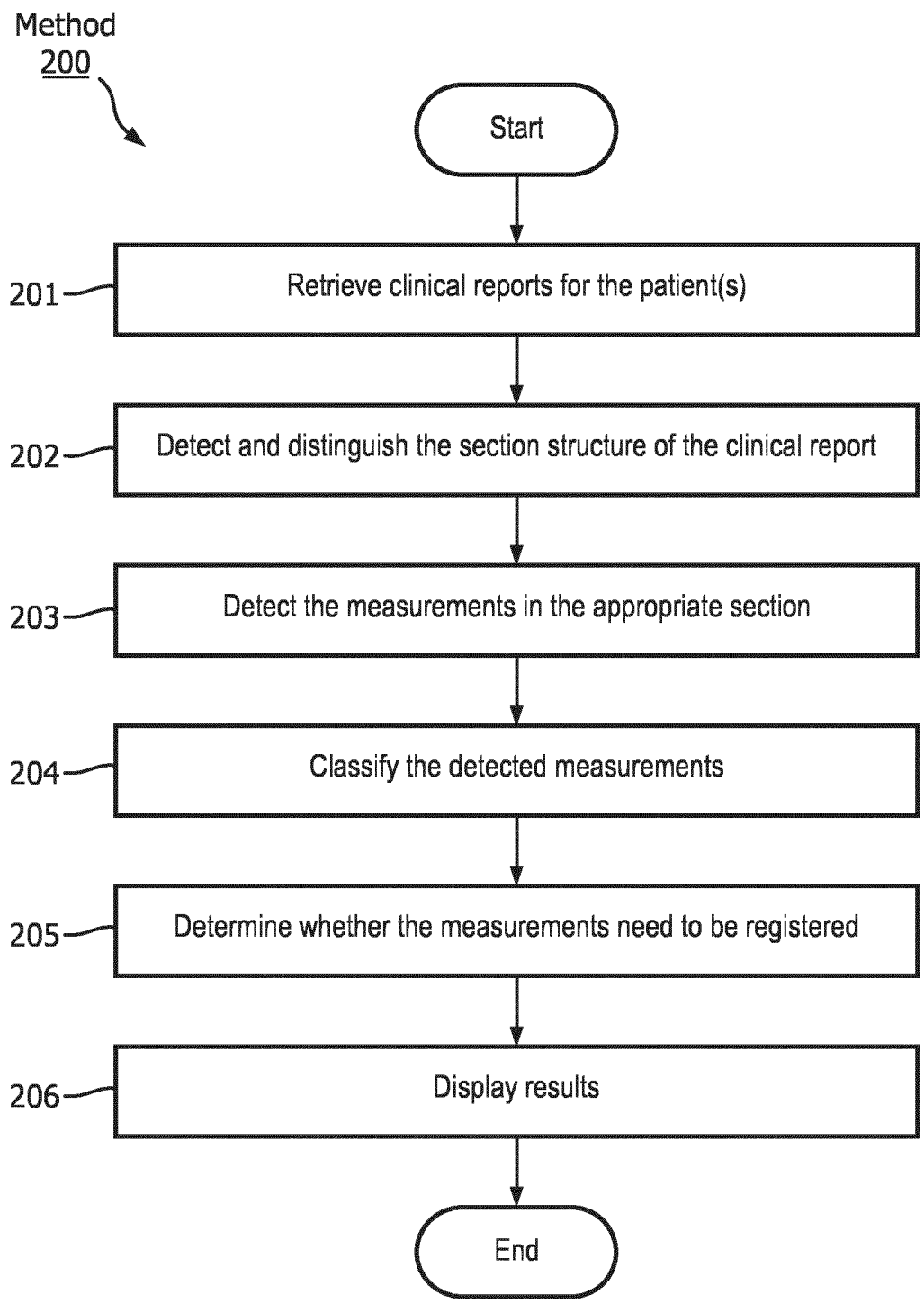
FIG. 2 shows a flow diagram of a method for determining the measurements that need to be registered, according to exemplary embodiments.

FIG. 2 shows a method 200 for determining the measurements that need to be registered. In particular, method 200 extracts and classifies the measurements from the clinical reports and updates the progress using the system 100. The method 200 comprises steps for retrieving and distinguishing clinical reports, detecting a section structure of the clinical reports, and recognizing and registering the measurements from the clinical reports.

In step 201, the acquisition engine 111 retrieves the clinical reports for the patient. For example, the clinical reports may be retrieved for the patient described above in the second exemplary use case. As discussed above, the clinical reports may be retrieved by transmitting the patient identifier through the API. It will be understood by those skilled in the art that step 201 may retrieve the clinical reports for multiple patients simultaneously.

In step 202, the extraction engine 112 detects the section structure of the clinical report. The extraction engine 112 may further distinguish the section structure. For example, a 'Findings' section may be distinguished from a 'Conclusion' section or any other sections included in the clinical report. In an exemplary embodiment, rule-based methods may be used to distinguish the section structure. For example, the rule-based methods may determine sentence markers, detect section headers and normalize the section headers onto a set of known document types. Those skilled in the art would understand that any number or type of sections may be distinguished.

In step 203, the extraction engine 112 detects the measurements in one or more of the sections, such as detecting measurements in the 'Findings' section. The extraction engine 112 may further distinguish different types of measurements. For example, the 'Findings' section may make reference to lesion measurements and aorta measurements. The extraction engine 112 distinguishes which measurements pertain to the lesions and which measurements pertain to the aorta, and detect the lesion measurements while ignoring the aorta measurements. It should be noted that the relevant lesions measurements are typically included in the 'Findings' section of clinical reports. However, there may be some radiology departments that organize the clinical reports in different manners. The extraction engine 112 may be trained to detect the measurements regardless of the particular section or portion of the clinical report that includes the measurements. In another example, pattern matching techniques may be used to detect measurements. The pattern matching techniques may use, for example, regular expressions to account for logistic variants in the way measurements are described. These linguistic variants may include variations within a single radiology department, variations based on geographical location, dialects, etc.

In step 204, the extraction engine 112 classifies the detected measurements. In one exemplary embodiment, the classifications may be in regards to the temporality of the measurements. For example, the clinical report may state "measures 1×2 cm on today's examination." This indicates the measurement refers to the correct clinical exam. In another example, the clinical report may state "previously measuring 1×2 cm." This indicates the measurement refers to a previous clinical exam. In a further example, the clinical report may state "stable with respect to the prior exam." This indicates the measurement refers to both the current clinical exam and a previous clinical exam. Thus, these examples show some manners of classifying the temporality of measurements. In another example, statistical or machine learning methods may be used to classify the temporality of measurements based on a linguistic context. Exemplary techniques for implementing the variants are further discussed in the following document, which is hereby incorporated by reference: M. Sevenster, J. Buurman, P. Liu, J. F. Peters, and P. J. Chang, "Natural Language Processing Techniques for Extracting and Categorizing Finding Measurements in Narrative Radiology Reports," Appl Clin Inf., vol. 6, no. 3 pp. 600-10, 2015.

Measurements may be classified in a scheme wherein top-level concepts identify the nature of the quantified entity: Clinical finding: The measurement describes the dimension(s) of a clinical finding. Relative position: The measurement characterizes the position of one entity with respect to the position of another. Technique specification: The measurement specifies an aspect of the image data or one of its reconstructions.

Clinical finding measurements ("finding measurements") may be subclassified into three classes: Current: The measurement refers to the current exam and not to the prior exam. Prior: The measurement refers to the prior exam and not to the current exam. Comparison: The measurement refers to both the current and the prior exam within the scope of the sentence in which it appears.

In step 205, the analytics engine 113 determines whether the measurements need to be registered. As discussed above in regards to FIG. 1, the analytics engine 113 may calculate the difference between the measurements count in the clinical report of the most recent clinical exam and subtract the measurements retrieved from the database 120 in regards to the clinical exam performed before the most recent clinical exam. If a difference is present, then measurements need to be registered.

For example, the analytics engine 113 may calculate a measurements count of three lesions in the clinical report of the patient's most recent clinical exam. The analytics engine 113 may then retrieve, from the database 120, a measurements count of two lesions from the clinical report of the clinical exam performed before the most recent clinical exam. It should be noted that the measurements retrieved from the database are already registered. The analytics engine 113 will then determine that since there are three lesions in the clinical report of the patient's most recent clinical exam and two lesions from the clinical report of the clinical exam performed before the most recent clinical exam, one lesion needs to be registered for the patient.

In step 206, the patient(s) with the measurements that need to be registered are displayed on the display 106. It should be noted that method 200 may be executed for a single patient or a plurality of the patients.

Figure 3:
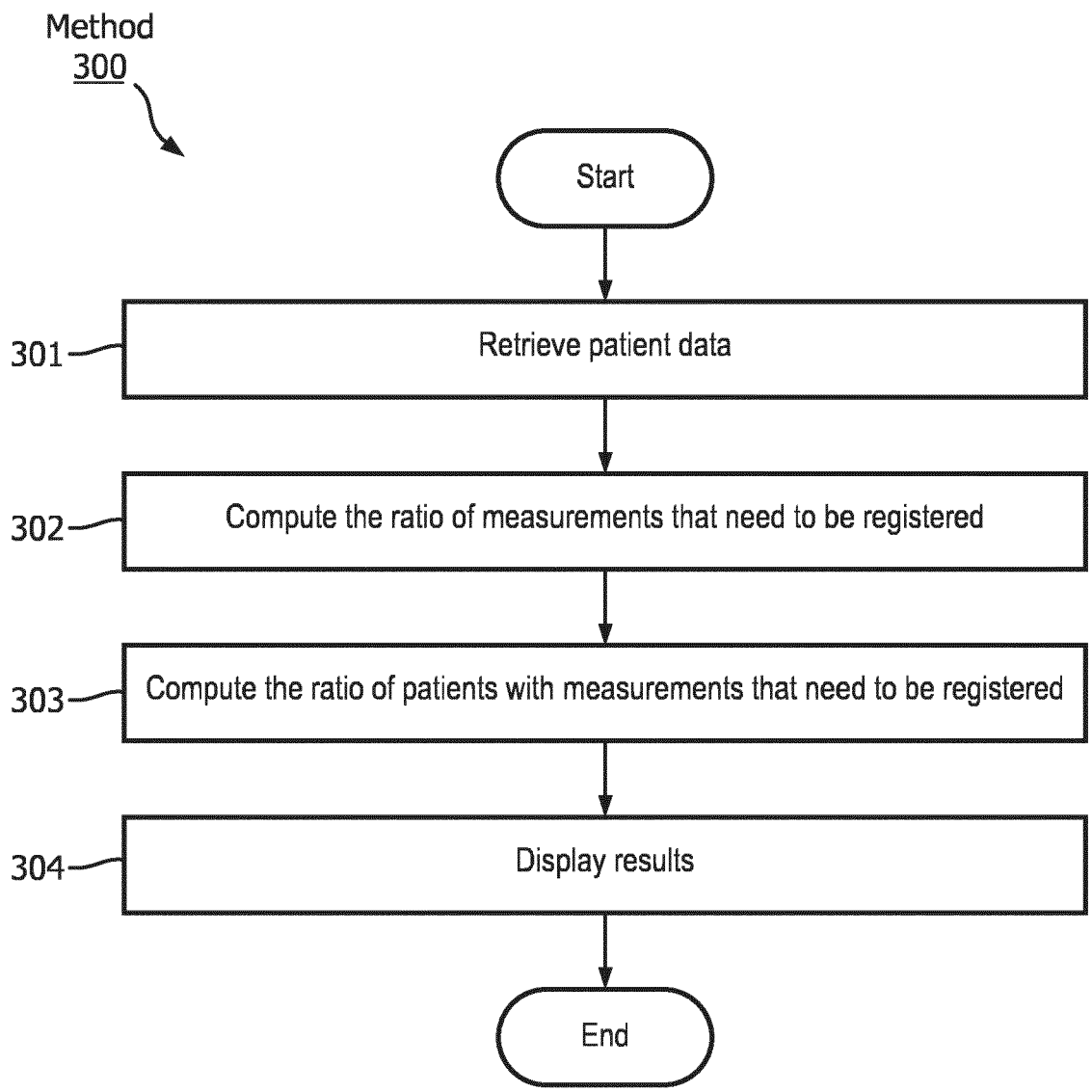
FIG. 3 shows a flow diagram of a method for assessing a progress of a user's efforts to register measurements, according to exemplary embodiments.

FIG. 3 shows a method 300 for assessing the progress of the user's efforts to register the measurements. In particular, method 300 determines the progress in terms of a percentage of the measurements that need to be registered and a percentage of cases that need to be bootstrapped.

In step 301, the analytics engine 113 retrieves data relating to the patient(s) with the measurements that need to be registered, for example, as conducted in method 200.

In step 302, the analytics engine 113 calculates the ratio of a number of measurements that need to be registered to a total number of measurements. To provide a specific example involving three patients and relating to the measurements being lesions, a first patient may have three lesions, two of which have been registered, a second patient may have two lesions, both of which have been registered, and a third patient may have four lesions, none of which have been registered. The analytics engine 113 would calculate that the total number of measurements (e.g. lesions) between the three patients is nine while the number of measurements that need to be registered is six. The analytics engine 113 would, therefore, further calculate that the ratio of the number of measurements that need to be registered to the total number of measurements is six measurements out of nine measurements (6/9).

In step 303, the analytics engine 113 computes the ratio of a number of patients with measurements that need to be registered to a total number of patients with measurements (e.g. a ratio of cases that need to be bootstrapped). Continuing the example involving the three patients discussed above, the analytics engine 113 may calculate that the first patient and the third patient have measurements that need to be registered, while the second patient has no measurements that need to be registered. The analytics engine 113 would, therefore, further calculate that the ratio of the number of patients with measurements that need to be registered to the total number of patients with measurements is two out of three (2/3). As such, two out of three cases need to be bootstrapped.

In step 304, the ratios are displayed on the display 106. It should be noted that either of the ratios can be narrowed by the time frame, as discussed above. The radiology department may use the results to understand the progress that is being made in registering imaging scans. The obvious goal is to reach 100% for each of the ratios in steps 302 and 303. However, the sheer quantity of measurements may make this goal very difficult to obtain. The measurements do allow the radiology department to set interim goals and determine how they are succeeding against the interim goals.

Figure 4:
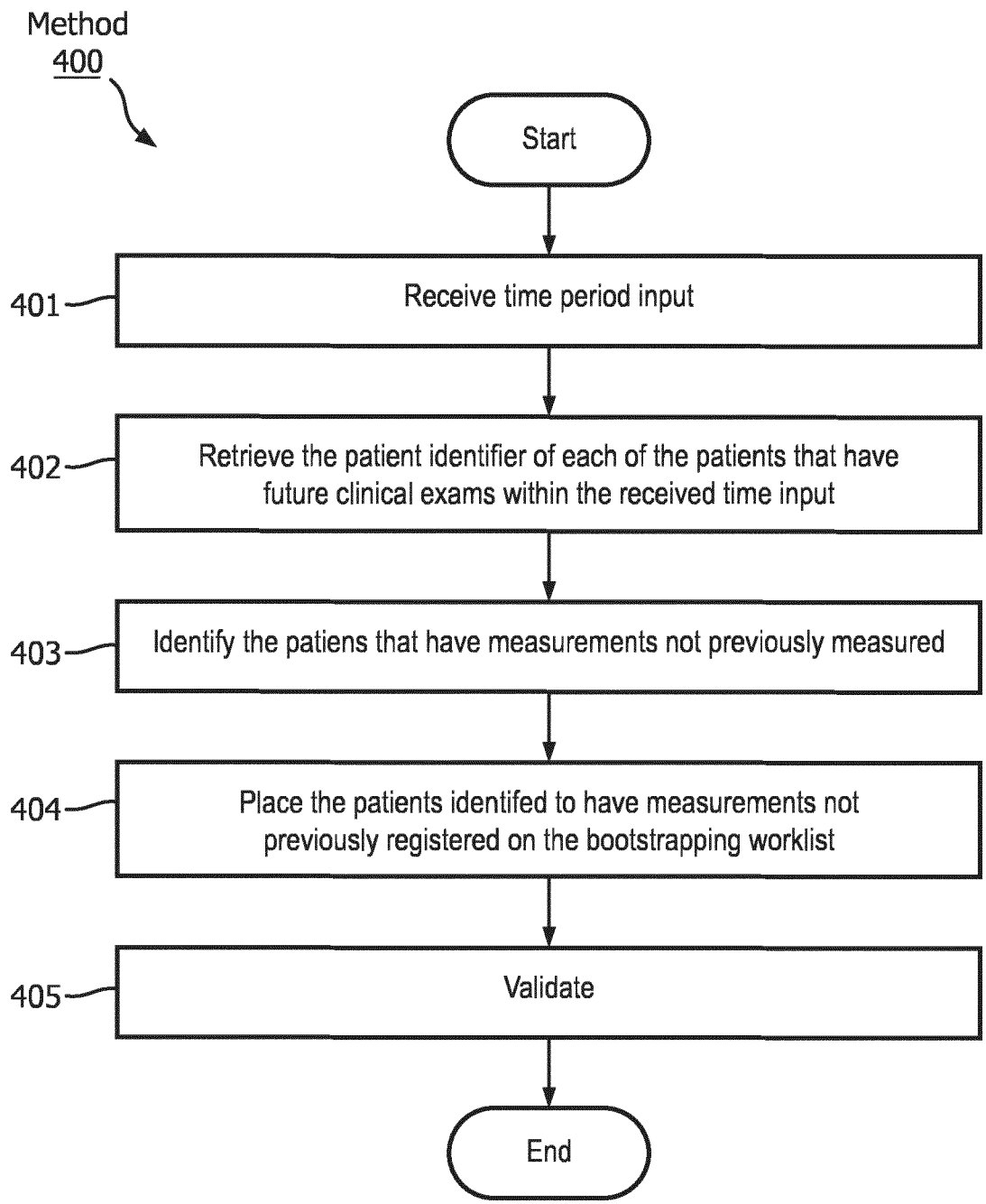
FIG. 4 shows a flow diagram of a method for generating a bootstrapping worklist, according to exemplary embodiments.

FIG. 4 shows a method 400 for generating the bootstrapping worklist regarding the cases to be bootstrapped. In particular, method 400 seeks to identify patients who have future clinical exams and the measurements of their previous clinical exams have yet to be registered.

In step 401, the user inputs a time period into the user interface 104. For example, the time period may be 12 hours, two days, one week, etc. In step 402, the worklist generation engine 114 retrieves the patient identifiers of the patients that have future clinical exams within the time period. The patient identifiers may be retrieved from the database 120.

In step 403, the worklist generation engine 114 identifies the patients whom have measurements that have not been registered. This may be done by the exemplary embodiments described in method 200 above. In step 404, the patients (e.g. via their patient identifiers) with measurements that have not been registered are placed on the bootstrapping worklist. In an exemplary embodiment, the bootstrapping worklist may be a spreadsheet file, which would facilitate easy sharing. Further, the bootstrapping worklist may be made available through document sharing technology.

At this stage, the user may use the bootstrapping worklist to bootstrap cases. In one variant, the user may manually mark the patients whose cases the user has bootstrapped. In another variant, the patients whose cases have been bootstrapped may be marked automatically. The worklist engine 114 may monitor for discrepancies between the extraction engine 112 and the database 120, either periodically or continuously, to update the bootstrapping worklist.

In step 405, the bootstrapped cases are validated. In particular, the compliance engine 115 consults the database 120 to validate that all of the measurements have been registered by the user in the structured format. If the measurement has been improperly registered, the compliance engine 115 may send an alert to the user. In the alternative, the compliance engine 115 may place the case with the improperly registered measurement(s) back onto the bootstrapping worklist.

Figure 5:
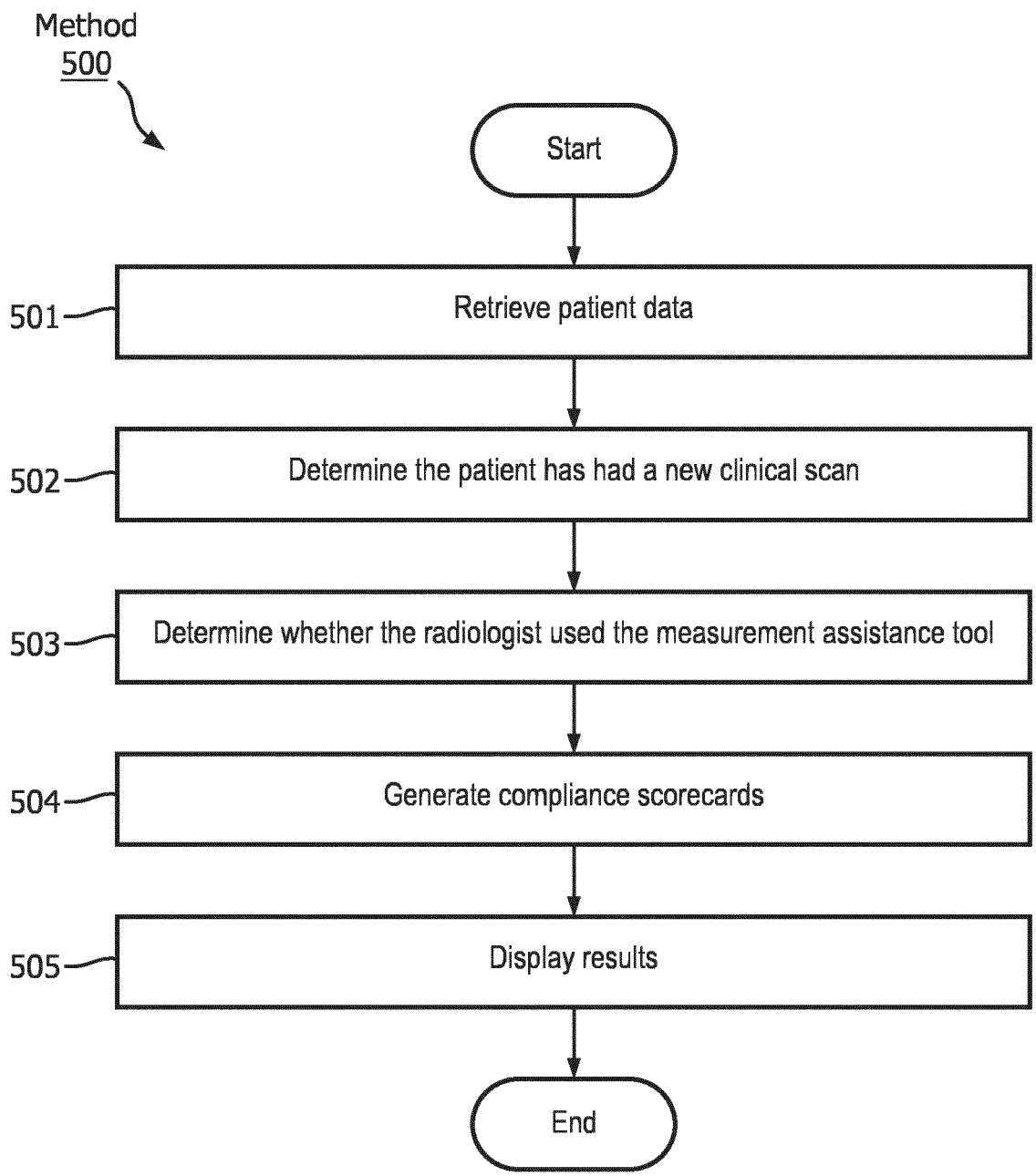
FIG. 5 shows a flow diagram of a method for monitoring a radiologist's compliance in utilizing a measurement assistant tool, according to exemplary embodiments.

FIG. 5 shows a method 500 for monitoring the radiologist's compliance in utilizing the measurement assistant tool. In particular, method 500 seeks to determine whether the radiologists used the measurement assistant tool for further clinical exams, (e.g., wherein the patient had newly discovered lesions, whether the measurements were registered in the structured format, etc.) and generate compliance scorecards for the radiologists. It should be noted that method 500 may be applied to individual radiologists, a group of radiologists, or the radiology department as a whole.

In step 501, the compliance engine 115 retrieves data relating to the patient(s) with the cases that have been bootstrapped, for example, as conducted in method 300. Further, the compliance engine 115 may retrieve data relating to the patient(s) which had all of their measurements registered. For example, continuing the example involving the three patients discussed above, the second patient has two lesions, both of which had been registered. As such, the compliance engine 115 may retrieve the second patient's case because the second patient has all of his measurements registered in the structured format.

In step 502, the compliance engine 115 determines whether the patient has had a new clinical scan. For example, the compliance engine 115 may consult the analytics engine 113 to determine if any clinical reports have been submitted after the patient's case has been bootstrapped. If yes, the compliance engine 115 may request the analytics engine 113 to determine whether the post-bootstrapped clinical report(s) contained new lesions. This may be accomplished by the steps disclosed in method 200.

In step 503, the compliance engine 115 determines whether the radiologist used the measurement assistance tool. For example, did the radiologist register the new lesions. In particular, the compliance engine 115 determines whether the new lesions have been registered in the structured format. On the other hand, if no new lesions are discovered, the compliance engine 115 may determine if the measurements from the new clinical scan have been entered in the structured format, indicating the radiologist used the measurement assistance tool.

In step 504, the compliance engine 115 generates the compliance scorecards. The compliance scorecards may track the percentage of clinical scans that have been registered using the measurement assistance tool (e.g., clinical scans that have registered been by the radiologist in the structured format). For example, the radiologist may have reviewed three clinical scans of three different patients. Further, the radiologist may use the measurements assistant tool to register (in the structured format) the measurements of two of the three patients while registering the measurements of the third patient in a non-structured format (e.g., using a voice recording). The compliance engine 115 would, therefore, produce a compliance scorecard indicating that the radiologist has a compliance score of 67%.

In step 505, the compliance scorecards may be viewed on the display 106. The scorecards may be public or private. In an exemplary embodiment, the scores of all but a viewing radiologist may be anonymized. This would show the viewing radiologist how he compares to his peer, while not disclosing the results of his peers. In one variant, only a staff member with administrative privileges may have access a master list of the radiologists and each of their corresponding scorecards. This would enable the staff member to make administrative decisions for each radiologist (e.g. discipline the radiologist, issue a bonus, etc.)

Those skilled in the art will understand that the above-described exemplary embodiments may be implemented in any number of manners, including, as a separate software module, as a combination of hardware and software, etc. For example, the acquisition engine 111, the extraction engine 112, the analytics engine 113, the worklist generation engine 114 and the compliance engine 115 may be programs containing lines of code that, when compiled, may be executed on a processor.

It is noted that the claims may include reference signs/numerals in accordance with PCT Rule 6.2(b). However, the present claims should not be considered to be limited to the exemplary embodiments corresponding to the reference signs/numerals.

It will be apparent to those skilled in the art that various modifications may be made to the disclosed exemplary embodiments and methods and alternatives without departing from the spirit or scope of the disclosure. Thus, it is intended that the present disclosure cover the modifications and variations provided that they come within the scope of the appended claims and their equivalents.

What is claimed is:

1. A method, comprising:
at an imaging system workstation:
retrieving a plurality of clinical reports for a plurality of patients;
detecting a measurement in each of the plurality of clinical reports;
detecting an identity of a radiologist that created each of the clinical reports;
determining a temporality of the detected measurements, wherein the temporality indicates whether each of the measurements are from a current imaging scan or a previous imaging scan, wherein the determining the temporality of the detected measurements is performed by statistical or machine learning methods;
determining which of the detected measurements have been registered in a defined structured format;
identifying one or more of the plurality of clinical reports that include measurements yet to be registered;
determining a ratio of registered measurements to yet to be registered measurements for each radiologist
placing the ratio for each radiologist on a compliance scorecard;
placing the one or more of the plurality of clinical reports on a worklist; and
registering the measurements in the defined structured format.

2. The method of claim 1, wherein the detecting is applied to at least one of a plurality of selected sections of the clinical reports.

3. The method of claim 1, wherein the retrieving is based on a selected time frame.

4. The method of claim 1, further comprising:
calculating a ratio of a number of the measurements that require registration to a total number of the measurements.

5. The method of claim 4, further comprising:
calculating a ratio of patients with measurements requiring registration to a total number of patients with measurements.

6. The method of claim 4, wherein the registration comprises utilizing a registration program capable to formatting the measurements into a structured format.

7. The method of claim 4, wherein the measurements are lesion measurements.

8. The method of claim 4, wherein the classifying detected measurements further includes a top-level concept identifying the nature of the measurement.

9. The method of claim 8, wherein the top-level concept identifying the nature of the measurement includes one of a clinical finding, a relative position, or a technique specification.

10. The method of claim 4, wherein retrieving the plurality of clinical reports comprises transmitting a patient's unique identifier through an Application Programming Interface (API).

11. The method of claim 10, wherein the API accesses a repository that contains the clinical reports.

12. The method of claim 10, wherein the API retrieves a master list of patient unique identifiers.

13. The method of claim 4, wherein the registered measurements and the yet to be registered measurements used in generating the ratio to be placed on the compliance scorecard is narrowed by a time frame.

* * * * *